United States Patent [19]

Hansen et al.

[11] Patent Number: 5,665,363

[45] Date of Patent: Sep. 9, 1997

[54] INOCULATION OF ANIMALS WITH DRIED, PELLETED BIOLOGICAL MATERIALS

[75] Inventors: Richard D. Hansen, Ankeny, Iowa; James F. Drake, Minneapolis, Minn.

[73] Assignee: InnoVac Co., Lincoln, Nebr.

[21] Appl. No.: 712,213

[22] Filed: Sep. 3, 1996

Related U.S. Application Data

[63] Continuation of Ser. No. 356,477, Dec. 15, 1994, abandoned, which is a continuation-in-part of Ser. No. 198,836, Feb. 18, 1994, abandoned.

[51] Int. Cl.$^6$ ............................................. A61K 39/155
[52] U.S. Cl. ........................... 424/211.1; 424/203.1; 424/279.1; 424/234.1
[58] Field of Search ................... 424/211.1, 234.1, 424/203.1, 229.1

[56] References Cited

U.S. PATENT DOCUMENTS

| | | | |
|---|---|---|---|
| 1,347,622 | 7/1920 | Deininger | 604/61 |
| 2,413,419 | 12/1946 | Saunders | 424/425 |
| 2,517,513 | 8/1950 | Vaernet | 424/424 |
| 2,705,214 | 3/1955 | Hink | 424/247.1 |
| 2,883,984 | 4/1959 | Canidido et al. | 604/61 |
| 3,072,121 | 1/1963 | Feldman | 604/57 |
| 3,402,712 | 9/1968 | Eisenhand | 604/61 |
| 3,744,493 | 7/1973 | Booher et al. | 604/62 |
| 3,774,607 | 11/1973 | Schmitz | 604/61 |
| 3,790,665 | 2/1974 | Glass | 424/78.31 |
| 3,830,907 | 8/1974 | Short | 424/425 |
| 3,919,411 | 11/1975 | Glass et al. | 424/78.27 |
| 3,975,350 | 8/1976 | Hudgin et al. | 524/108 |
| 3,982,536 | 9/1976 | Kregseng et al. | 424/422 |
| 4,077,406 | 3/1978 | Sandhage et al. | 604/61 |
| 4,105,030 | 8/1978 | Kercso | 604/49 |
| 4,154,239 | 5/1979 | Turley | 604/61 |
| 4,223,674 | 9/1980 | Fluent et al. | 604/51 |
| 4,292,307 | 9/1981 | Zemlykova | 424/239.1 |
| 4,325,524 | 4/1982 | Drake, Jr. et al. | 246/34 R |
| 4,326,523 | 4/1982 | Wolfrom et al. | 424/426 |
| 4,400,170 | 8/1983 | McNaughton et al. | 604/62 |
| 4,531,938 | 7/1985 | Kaye et al. | 604/62 |
| 4,576,591 | 3/1986 | Kaye et al. | 604/62 |
| 4,762,515 | 8/1988 | Grimm | 604/61 |
| 4,842,862 | 6/1989 | Jacobs et al. | 424/422 |
| 4,863,736 | 9/1989 | Azain et al. | 424/423 |
| 4,917,685 | 4/1990 | Viswanathan et al. | 604/891.1 |
| 5,238,928 | 8/1993 | Berger et al. | 514/179 |
| 5,288,496 | 2/1994 | Lewis | 424/426 |
| 5,342,622 | 8/1994 | Williams et al. | 425/425 |

FOREIGN PATENT DOCUMENTS

| | | |
|---|---|---|
| WO 87/06129 | 10/1987 | WIPO. |
| WO 87/06828 | 11/1987 | WIPO. |
| WO 92/17165 | 10/1992 | WIPO. |

OTHER PUBLICATIONS

Derwent Publications Ltd., London, GB; AN 90–015187 & ZA,A,8 809 601 (Burger), dated 25 Oct. 1989. (Abstract only).

Derwent Publications Ltd., London, GB; AN 93–025289 & SU,A, 1 713 584 (Moscow Agricultural Acad.), dated 23 Feb. 1992. (Abstract only).

Derwent Publications Ltd., GB; AN 83–46442k & SU,A, 940715 (Animal Husb. Res. Inst.), 7 Jul. 1982. (Abstract only).

H.F. Hass, *Potency Testing of Cl. Sordellii Bacterin–Toxoids by Mean of a Mouse Protection Test*, Joint OIE–IABS Symposium on Clostridial Products in Veterinary Medicine, Paris 1975, Develop. biol. Standard, vol. 32, pp. 167–172 (1976).

*Animals and Animal Products*, Code of Federal Regulations, vol. 9, pp. 563–571, (Jan. 1993).

Jones et al., *Organs of Special Sense*, Veterinary Pathology, 5th Ed., pp. 1724–1725, (1983).

Schrag, *Healthy Calves–Healthy Cattle: the most important diseases is rearing and fattening: recognition, prevention, treatment*, Hengersberg, West Germany (1982). p. 14.

Rosenberger, *Clinical Examination of Cattle*, p. 416, (1979).

Radositits et al., *A Textbook of the Diseases of Cattle, Sheep, Pigs, Goats and Horses*, Veterinary Medicine, 8th Ed. (1994).

Smith, *Future of Animal–Health Technology*, National Cattlemen (Sep. 1994) pp. 6–7.

Eichhorn et al., *Studies in Blackleg Immunization With Special Reference to Blackleg Filtrate*, JAVMA, vol. 15, pp. 652–669 (1918).

Heckhard, *Blackleg (As I Diagnosed It) Vaccinating and Results*, American Veterinary Review, vol. 39, pp. 440–443 (1911).

Hartman, *Blackleg*, JAVMA, vol. 3, pp. 618–620, (1917).

Nitta, *Investigating on Blackleg Immunization*, JAVMA, vol. 6, pp. 467–483, (1918).

Brochure, ALPHA–7, Boehringer Ingelheim Animal Health, Inc. (1994).

*Primary Examiner*—James C. Housel
*Assistant Examiner*—Ginny Allen Portner
*Attorney, Agent, or Firm*—Merchant, Gould, Smith, Edell, Welter & Schmidt, P.A.

[57] ABSTRACT

A method for vaccinating an animal by implanting subcutaneously an immune stimulating biologically active material into an animal with a biologically active pellet is described. Particularly described is the method of vaccinating an animal by implanting the pellet in the ear of an animal to eliminate edible tissue damage without inducing a "drooped ear" or "down ear".

9 Claims, No Drawings

INOCULATION OF ANIMALS WITH DRIED, PELLETED BIOLOGICAL MATERIALS

CROSS-REFERENCE TO RELATION APPLICATION

This is a continuation of application Ser. No. 08/356,477, filed Dec. 12, 1994 now abandoned, which is a continuation-in-part of Ser. No. 08/198,836 filed Feb. 18, 1994 now abandoned.

The licensing of veterinary biological products in the United States is governed by the United States Department of Agriculture (USDA) in contrast to the approval by the Food and Drug Administration (FDA) of drug substances administered to animals.

FIELD OF THE INVENTION

The invention relates to the inoculation of living animals. More particularly, the invention relates to a biologically active pellet containing a biologically active material and a method for conveniently implanting the biologically active pellet subcutaneously into the animal.

BACKGROUND OF THE INVENTION

The vaccination of domestic and wild animals is well known. Vaccination is normally performed by injection of a vaccine in liquid form from a syringe. Multiple inoculations are sometimes necessary to achieve a desired effect, due to the inability of the animal's body to respond immunologically to the biologically active ingredient after a single application.

An important disadvantage in administering liquid biologically active materials by syringe involves the preparation of the biologically active materials immediately prior to usage. The biologically active materials are often manufactured in concentrated, freeze-dried form and must be reconstituted prior to use of the biologically active material. Also, all liquid biologicals require shaking prior to and during usage. If the product contains live organisms, the dried biological is usually more stabile than the liquid form and can be shipped and stored under refrigerated conditions until reconstituted for use.

When prepared for use in the animal, the user may reconstitute the above biologically active material with a sterile liquid provided by the manufacturer. The reconstituted biologically active materials must be used within a short period of time and the remainder discarded because of their poor shelf life. When reconstitution is not necessary, the user must still shake the biologically active material before and during use. While the quality of the dried biologically active material can be carefully controlled by the manufacturer, the quality and dosage accuracy of the reconstituted biologically active material or the liquid ready-to-use biological active material is limited by the care exercised by the ultimate user.

To solve the above problem as well as the problem of disposing of used needles, syringes and unused contaminated biological products, biodegradable ballistic projectiles containing freeze-dried biologically active materials for intramuscular implantation into living animal bodies were invented. The nature of the ballistic projectiles has been disclosed in U.S. Pat. No. 3,948,263, U.S. Pat. No. 3,982,536, U.S. Pat. No. 4,449,982 and U.S. Pat. No. 4,664,664. These implants generally comprise a non-lethal polymeric projectile having an interior cavity containing freeze-dried, pelleted biologically active material. U.S. Pat. No. 4,326, 524 comprises a solid dosage projectile entirely formed of biologically active material.

There is an ever-increasing demand by consumers for a healthful food supply. The beef industry, as voiced by the membership of the National Cattlemen's Association, is "dedicated to improvement of the total quality of the product they produce" and resolves to "encourage the entire beef industry to work promptly toward a goal of increasing the number of animal health products that can effectively and properly be administered in locations other than lean tissue". These statements of policy resulted from the discovery that injection of some biologicals and pharmaceuticals into lean tissue causes lasting blemishes. These blemishes, although not a health threat to consumers, are a cosmetic problem that often result in a trim loss. Manufacturers of biologicals, in particular, have responded to the problem by recommending their products be administered subcutaneously in the neck and shoulder region or have developed lower volume, "less reactive" products for use by either the intramuscular or subcutaneous route. Those biologicals which are licensed only for intramuscular use are increasingly being recommended for neck-site injection to move the products out of the "prime cuts"

Proper subcutaneous administration of biologicals in the neck region can be very difficult if cattle are chute-processed and often are placed inappropriately. Even if proper placement is achieved, persistent subcutaneous swellings still often result, sometimes involving the hide and/or the underlying edible tissue. Due to the known irritant nature of injectable biologicals, particularly, those containing oils or aluminum salts in liquid suspensions, administration of such in the ear of cattle likely causes substantial tissue reactivity which can result in a "drooped" or "down ear". Thus, a substantial need exists for a system that can deliver biologically active materials in a manner that eliminates lean tissue damage to the animal following vaccination without other undesirable effects.

SUMMARY OF THE INVENTION

Accordingly, the present invention is directed to a method for vaccinating an animal with a biologically active material comprising the step of implanting a biologically active pellet comprising an effective immune stimulating amount of a biologically active material subcutaneously into the animal.

In a preferred embodiment, the invention is directed to a method for vaccinating an animal with a biologically active material, the method comprising the step of implanting a biologically active pellet subcutaneously into an ear of an animal with an implant gun wherein the biologically active pellet comprises:

(a) about 45 to 97% by weight of an immune stimulating biologically active material;

(b) about 2 to 40% by weight of freeze-drying excipient; and (c) about 0.2 to 5% by weight of a lubricant, wherein the method does not cause sufficient tissue irritation to produce a "drooped ear" or "down ear" in the animal.

A "drooped" or "down" ear is considered undesirable to the industry since it can be misinterpreted as a sign of underlying systemic disease. Multiple etiologies can manifest themselves or carry with them an associated down or drooped ear. Howard et al. in *Current Veterinary Therapy in Food Animal Medicine 1st Edition* lists: Bovine Respirator Complex (BRDC), Listeriosis, Pasturellosis, Otitis Externa, Otitis Media and facial nerve paralysis. *Veterinary Pathology 5th Edition* by Jones and Hunt also lists: Otomycosis, foreign body obstruction of the external ear canal, parasitic infection of the external ear and neoplasms. Clinical observation in cases involving auricular implant abscission, head trauma and traumatic reticulopericarditis have also been made.

The genetics of the animal can affect the value of the drooped or down ear clinical observation. Cattle with Zebu influence naturally have ears that hang. This makes determination of a down or drooped ear much more difficult in them as compared to other breeds of cattle.

In an alternative embodiment, the invention is directed to a biologically active pellet comprising about 76.5 to 96.5% by weight of an immune stimulating biologically active material, about 3 to 20% by weight of a freeze-drying excipient and about 0.5 to 3.5% by weight of a lubricant.

The invention results in a method of inoculating an animal which significantly minimizes tissue damage to the animal associated with the delivery of the biologically active material. Furthermore, the method of the invention is compatible with standard pellet implanting devices such as Ivy's IMPLUS™ Implanter and other marketed pharmaceutical pellet implanters which when applied to the administration of biologicals reduce disposal of syringe and needle waste. Additionally, the biologically active material is delivered to the animal in a pre-measured effective dosage which requires no pre-blending or shaking of the biologically active material prior to implantation into the animal.

DETAILED DESCRIPTION OF THE INVENTION

In general, the invention is directed to a method for vaccinating an animal with a biologically active material comprising the step of implanting a biologically active pellet subcutaneously into the animal. A biologically active material is any USDA-licensed material which stimulates an immune response in the animal. Specifically, the biologically active material, when administered to the animal, will cause the formation of antibodies or induce other resistance mechanisms by the animal.

Viruses (live or killed), bacteria (live or killed), protozoa (live or killed) and detoxified toxins are all well known biologically active materials and particularly useful ingredients in vaccines, bacterins, toxoids and bacterin-toxoids used to protect animals against specific diseases.

Vaccines can comprise either a killed or living virus. A killed vaccine can comprise wild (pathogenic) or attenuated viruses while living vaccines usually are comprised of attenuated viruses. Vaccines can also be comprised of living bacteria. Bacterins can comprise killed bacteria. Toxoids are biologically active materials included alone as immunogens. Bacterin-toxoids are a suspension of killed bacteria along with toxoids.

A representative list of biologically active materials which can be used in the practice of the invention include: infectious bovine rhinotracheitis virus, bovine viral diarrhea virus, bovine parainfluenza 3 virus, bovine respiratory syncytial virus, *Haemophilus somnus, Pasteurella haemolytica, Pasteurella multocida, Leptospira Spp., Campylobacter fetus, Clostridium spp.*, rotavirus, coronavirus, *Escherichia coli, Moraxella bovis, Bordetella bronchiseptica, Erysipelothrix rhusiopathiae, Actinobacillus pleuropneumoniae, Mycoplasma hyopneumoniae, Mycoplasma bovis, Mycoplasma dispar*, porcine parvovirus, transmissible gastroenteritis virus, pseudorabies virus, *Salmonella spp.*, canine parvovirus, canine adenovirus, canine distemper, canine parainfluenza, rabies, feline leukemia, feline vital rhinotracheitis, feline calivirus, feline panleukopenia, and *Chlamydia psittaci.*

Preferably, the biologically active material is selected from the group consisting of *Clostridium chauvoei, Clostridium septicium, Clostridium novyi, Clostridium sordellii*, and *Clostridium perfringens* and mixtures thereof. In an alternative embodiment, the biologically active material is selected from the group consisting of *Clostridium perfringens* bacterin-toxoids and mixtures thereof.

The biologically active pellets comprise an effective immune stimulating amount of a biologically active material. Preferably, the biologically active pellet comprises about 45 to 97% by weight of a biologically active material. More preferably, the biologically active pellet comprises about 50 to 85% by weight of a biologically active material, most preferably 60 to 75% by weight.

In the practice of the invention, the biologically active materials may be manufactured by known methods and may generally be purchased from well known USDA-licensed manufacturers. The liquid form of the biologically active material is dried by known methods, for example, freeze-dried or spray-dried. Typically, but not universally, a liquid suspension of the biologically active material adsorbed on aluminum hydroxide gel is mixed with a freeze-drying excipient and this mixture of biologically active material/freeze-drying excipient is then freeze-dried (lyophilized). The dried powder is then processed to reduce the particle size and sufficient lubricant is added to form a powder blend. Finally, the powder blend is then pelletized on a conventional pelletizing machine to produce the biologically active pellet.

The freeze-drying excipient is added to the biologically active material prior to freeze-drying to help make the powder resulting from the freeze-drying process sticky. Generally, the freeze-drying excipients also help to stabilize biologically active material during the freezing and lyophilizing processes.

A list of freeze-drying excipients that can be used in the practice of the invention includes but should not be limited to mannitol, lactose, trehalose, glucose, glycine, calcium lactobionate, calcium gluconate, dextran, glycerol, dried milk solids, serum albumins and mixtures thereof. Preferably, the freeze-drying excipient contains mannitol.

Generally, an effective amount of a freeze-drying excipient is utilized to make the powder resulting from the freeze-drying process sticky. Preferably, the biologically active pellet comprises about 2 to 40% by weight of a freeze-drying excipient. More preferably, the biologically active pellet comprises about 3 to 20% by weight of the freeze-drying excipient, most preferably about 4 to 10% by weight.

After the freeze-drying process is completed, and a dried powder mixture of the biologically active material/freeze drying excipient is achieved, the dried powder mixture is then blended with a lubricant and pelletized into final form. Lubricants facilitate the release of the pellets from the pelleting dies.

A list of lubricants that can be used in the practice of the invention includes but should not be limited to, magnesium stearate, calcium stearate, sodium stearyl fumarate, stearic acid, sodium lauryl sulfonate, polyoxyethylene (carbowaxes), polyethylene glycols, glycerol behenate, hydrogenated vegetable oils and mixtures thereof. Preferably, the lubricant contains calcium stearate.

Generally, the biologically active pellet comprises an effective pellet-forming amount of a lubricant. Preferably, the biologically active pellet comprises about 0.2 to 5% by weight of a lubricant. More preferably, the biologically active pellet comprises about 0.5 to 3.5% by weight of a lubricant, most preferably about 1.0% by weight.

TABLE 1

| | % By Weight of the Biologically Active Pellet | | |
| --- | --- | --- | --- |
| | Useful Range | Working Range | Preferred Range |
| Biologically active Material | 45–97 | 50–85 | 60–75 |
| Freeze-Drying Excipient | 2–40 | 3–20 | 4–10 |
| Lubricant | 0.2–5 | 0.5–3.5 | 1.0–2.0 |

Optionally, the biologically active pellet can comprise additional excipients. These additional excipients can be added to the biologically active pellet to provide increased strength, to control solution times, to improve powder handling, e.g. flow and the like, or to improve the efficacy of the product. A list of additional excipients that can be used in the biologically active pellet of the invention includes but should not be limited to: precipitated or fumed silicas, sodium starch glycolates, calcium phosphates, calcium carbonate, dextrins, polyvinyl pyrrolidone, hydroxypropylcellulose, hydroxypropylmethylcellulose, polylactic acid, polyglycolic acid, magnesium aluminum silicates, microcrystalline cellulose, sodium carboxymethyl cellulose and mixtures thereof. Preferably, these additional than about 50% less than about 50% by weight of the biologically active pellet. More preferably, these additional excipients constitute less than about 40% by weight of the biologically active pellet, most preferably 25% by weight.

Pellets may be generally prepared as follows:

A liquid suspension containing bacterial cells and associated products adsorbed on aluminum hydroxide gel is mixed with sufficient mannitol to yield a final weight of 65 milligrams per dose of product. The suspension is dispensed into containers, frozen, and the water removed under vacuum. After freeze drying is complete, the dried powder is harvested. The powder is processed to reduce the particle size to less than 0.1 millimeter and sufficient calcium stearate (approximately 1% by weight) is added for lubrication.

The powder blend is then tabletted on a conventional tabletting machine to produce uniform pellets. A typical formulation for the above pellets would be:

| | |
| --- | --- |
| Freeze-dried powder 65 | (Powder has 34 parts bacterial cells and 31 parts mannitol) |
| Calcium stearate 1 | |
| Precipitated silica 0.3 | |

Pellets produced as above may, if desired, be converted to delayed release pellets by coating with materials that will delay the escape of the material to the body. Materials that are useful for this are compounds that will slowly degrade or dissolve in the body fluids. Examples of materials suitable for use are hydrolytically unstable polymers such as polylactic acid, polymers such as ethylvinyl acetate that are slow to dissolve in body fluids, or waxy solids, such as cholesterol, that have a limited solubility in aqueous fluids. These materials can be applied to the tablet as coatings and will act to delay the release of the active ingredient from the pellet.

There are a number of coating techniques available for adding the delayed release coatings to the pellets. Rotating drum coaters or fluidized bed coating processes can be used. Any process that can apply a uniform coating in a controlled manner can be used. The thickness of the coating and water solubility will determine the delay before the product is released.

The biologically active pellets of the invention can be formed into any possible shape that the pelletizing machine is capable of making. Preferably, the shape and size of the biologically active pellet is suitable for implanting into the animal. More preferably, the shape of the biologically active pellet is such that it can be used in conjunction with an implant gun such as Ivy's IMPLUS™ Implanter or other marketed pharmaceutical pellet implanters. Most preferably, the shape and size of the pellet is adapted for implanting the biologically active pellet subcutaneously into an ear of the animal.

In general, the size of the biologically active pellet depends on the dose to be administered to the animal and compatibility with the implant gun used.

The biologically active pellets of the invention can be implanted into any animal which is capable of exhibiting an immune response from the biologically active material. Generally, these animals include but should not be limited to cattle, hogs, horses, cats, dogs, sheep, goats, for example. In a preferred embodiment of the invention, the animal is domestic cattle.

The biologically active pellets can be implanted into the animal by any means which non-ballistically implant the biologically active pellets subcutaneously in the animal. Preferably, the delivery device is an implant gun described by U.S. Pat. No. 4,762,515, manufactured by Ivy Laboratories, Inc. of Overland Park, Kan.

The biologically active pellet can be subcutaneously implanted into any area of the animal which allows the biologically active pellet to come into contact with tissue fluids. Preferably, the biologically active pellet is implanted into an area of the animal which minimizes or eliminates lasting damage to edible tissue of the animal. More preferably, the biologically active pellet is implanted into an ear, the neck, the tail-head or flank areas of the animal thereby reducing potential damage to edible tissue. Most preferably, the biologically active pellet is implanted into an ear of the animal, thereby eliminating damage to edible tissue. Surprisingly, we have found that implanting the biologically active pellet into an ear of the animal does not result in an undesirable "drooped ear", or "down ear" in the animal. As with any product administered through the skin, sanitary methods must be followed to reduce the likelihood of injection site infections/abscesses which may result in undesirable local tissue reactions.

Veterinary biologicals, particularly clostridial products, can be very tissue reactive and can cause lasting damage to lean tissue or can cause large subcutaneous enlargements that persist and can affect the hide and underlying muscle. Placement of pelleted, low volume biologicals subcutaneously, particularly in the ear appears to be a safe practice that should be acceptable to the beef industry.

The following Examples are provided as illustrative but not limiting of the present invention.

EXAMPLE 1

Sixteen liters of a formalin-treated, aluminum hydroxide adsorbed preparation of bacteria and bacterial culture fluids derived from *Clostridium chauvoei*, *Clostridium septicium*, *Clostridium novyi*, *Clostridium sordellii*, and *Clostridium perfringens* cultures are blended with 0.125 liters of sterile 30% mannitol solution. The mixture is dispensed into shallow pans. The pans are then loaded into a large vacuum chamber with temperature controlled shelves and frozen at −50° C. The chamber is then evacuated and the temperature of the frozen material is raised to −10° C. The temperature is maintained until substantially all of the water has sublimed. The dry product is then passed through a screen with a mesh size of 0.033 inches in order to reduce the particle size. Sterile calcium stearate (1.0%) is added as a lubricant. Sterile high surface area silicon dioxide (0.4%) is added to improve the flowability of the powder. The blended powder is then formed into pellets on a pharmaceutical tabletting press. The resulting pellets, when tested for potency in laboratory animals according to Standard 9 CFR or USDA filed Production Outline Methods, are highly protective against the effects of infections caused by *Clostridium chauvoei, Clostridium septicium, Clostridium novyi, Clostridium sordellii, Clostridium perfringens* Type C and *Clostridium perfringens* Type D. The results of the testing is illustrated as follows:

TABLE 2

| Bacterin-Toxoid Fraction | USDA Requirement | Level Attained (Example 1 Product) |
|---|---|---|
| *Clostridium Chauvoei* | ≧7 of 8 test animals survive[1] | 8 of 8 test animals survived |
| *Clostridium Septicum* | ≧1.0 IU[2] | 4 Units < 5 Units |
| *Clostridium Novyi* | ≧0.5 IU[2] | 0.5 Unit < 1.0 Unit |
| *Clostridium Sordellii* | ≧1.0 IU[2] | 5 Units < 10 Units |
| *Clostridium Perfringens* Type C | ≧10 IU[2] | 30 Units < 50 Units |
| *Clostridium Perfringens* Type D | ≧2 IU[2] | 4 Units < 6 Units |

[1]To pass Stage 1 test.
[2]International Units.

The resulting pellets were tested in cattle for *Clostridium Chauvoei* efficacy according to a USDA-accepted protocol. Ten (10) susceptible calves were vaccinated subcutaneously twice by the neck route with the product of Example 1. An additional 10 comparable calves were vaccinated subcutaneously with the product of Example 1 twice via the ear route. A third group of 10 contemporary calves were left unvaccinated and allowed to commingle with the vaccinates until intramuscular challenge with virulent *Clostridium chauvoei*. Challenge of all 30 calves occurred 46 days after the second vaccination. The following is a summary of the post-challenge results:

TABLE 3

| Cattle Group | Mortality Following Challenge |
|---|---|
| Neck Vaccinates | 0 of 10 |
| Ear Vaccinates | 0 of 10 |
| Unvaccinated Controls | 10 of 10 |

EXAMPLE 2

Seventeen liters of a formalin-treated, aluminum hydroxide adsorbed preparation of *Clostridium perfringens* culture fluids are blended with 3.63 liters of sterile, 30% w/v mannitol. The mixture is dispensed into shallow pans, frozen at −50° C., and dried under a vacuum as in Example 1. The resulting dry powder is sized and then blended with sterile calcium stearate (1.5%), and sterile high surface area silicon dioxide (0.5%). The blended powder is then tabletted on a 14 station tabletting press with ⅛ inch diameter dies to produce pellets with an average length of 0.15 inches. The resulting pellets when tested for potency according to Standard 9 CFR Methods yielded the following results:

TABLE 4

| Bacterin-Toxoid Fraction | USDA Requirement | Level Attained (Example 2 Product) |
|---|---|---|
| *Clostridium Perfringens* Type C | ≧10 IU[1] | 50 Units < 70 Units |
| *Clostridium Perfringens* Type D | ≧2 IU[1] | 8 Units < 10 units |

[1]International Units

Field Safety Trials

Pellets containing *Clostridium Perfringens* prepared according to Example 2, were administered using the IMPLUS™ Implanter in three field safety trials in a total of 359 calves ranging in age between 6 and 12 months. The product was administered subcutaneously in the back side of the ear. Booster vaccinations occurred in the opposite ear, with the exception of one animal in the Wyoming trial. Calf. #103 had only 1 ear, so the second vaccination was separated from the first by spacing them. Needles were disinfected and dried between each usage whenever possible.

Vaccinated animals were observed for at least 1 hour following each vaccination for signs of acute anaphylactoid reactions. Gross observations of the cattle occurred daily, especially noting whether the product induced a swelling sufficient to create a "down ear". Initial vaccination sites were palpated at the time of booster vaccination and results recorded on supplied observation sheets. A final palpation of the vaccination sites occurred at least 14 days following the second vaccination. Dimensions of the swellings, if they occurred, were measured in centimeters. A grading system was applied to group like-sized swellings:

Grade 0: No lesion palpable.

Grade 1: All dimensions of swelling ≦1.5 cm.

Grade 2: Greatest dimension of swelling between 2.0 and 2.5 cm.

Grade 3: Greatest dimension of swelling between 3.0 and 3.5 cm.

Grade 4: Greatest dimension of swelling between 4.0 and 4.5 cm.

Grade 5: Greatest dimension of swelling ≧5.0 cm.

No acute anaphylactoid reactions occurred in any vaccinate, as reported in Table 5.

In Oklahoma, 94 calves were administered the initial dose of the product. Three (3) calves (#78, 83, 93) died of bovine respiratory disease (BRD) before the second vaccination. Two (2) additional calves (#30, 74) died of BRD after the second vaccination but before the final site palpation. Therefore, 89 calves from the 2 groups remained in the group at the end of the study.

In Wyoming, 115 head were to be included in the trial. One (1) animal needed to be moved to a "buller pen" after the initial vaccination and was not followed after this.

Results of local tissue observations are summarized in Table 6. No "down ear" problems occurred in any animal as a result of post-vaccination swelling. A single down ear in calf #30 was observed in the Oklahoma trial. This condition was found to be unrelated to the experimental product vaccination. This animal died of bovine respiratory disease during the trial.

TABLE 5

FIELD TRIAL SUMMARY OF ACUTE REACTIONS

| STATE | NO. OF CATTLE | ADVERSE ACUTE REACTIONS |
|---|---|---|
| Nebraska | 150 | None |
| Oklahoma | 94 | None |
| Wyoming | 115 | None |
| Total | 359 | |

TABLE 6

POST-VACCINATION SITE OBSERVATIONS

| TRIAL | VACCINATION 1 SITE (#AFFECTED/TOTAL) | VACCINATION 2 SITE(# AFFECTED/TOTAL) |
|---|---|---|
| Nebraska | 31 DAYS | 45 DAYS | 14 DAYS |
| | Grade 0: 61/150 | Grade 0: 87/150 | Grade 0: 106/150 |
| | Grade 1: 51/150 | Grade 1: 46/150 | Grade 1: 31/150 |
| | Grade 2: 27/150 | Grade 2: 15/150 | Grade 2: 9/150 |
| | Grade 3: 10/150 | Grade 3: 2/150 | Grade 3: 3/150 |
| | Grade 4: 1/150 | Grade 4: 0/150 | Grade 4: 1/150 |
| | Grade 5: 0/150 | Grade 5: 0/150 | Grade 5: 0/150 |
| Oklahoma (Group 1) | 29 DAYS | 29 DAYS |
| | Grade 0: 18/47 | Grade 0: 14/46 |
| | Grade 1: 25/47 | Grade 1: 22/46 |
| | Grade 2: 4/47 | Grade 2: 9/46 |
| | Grade 3: 0/47 | Grade 3: 1/46 |
| | Grade 4: 0/47 | Grade 4: 0/46 |
| | Grade 5: 0/47 | Grade 5: 0/46 |
| Oklahoma (Group 2) | 30 DAYS | 21 DAYS |
| | Grade 0: 10/44 | Grade 0: 14/43 |
| | Grade 1: 13/44 | Grade 1: 25/43 |
| | Grade 2: 13/44 | Grade 2: 2/43 |
| | Grade 3: 8/44 | Grade 3: 2/43 |
| | Grade 4: 0/44 | Grade 4: 0/43 |
| | Grade 5: 0/44 | Grade 5: 0/43 |
| Wyoming | 37 DAYS | 23 DAYS |
| | Grade 0: 23/114* | Grade 0: 48/114** |
| | Grade 1: 44/114**** | Grade 1: 49/114* |
| | Grade 2: 33/114* | Grade 2: 11/114 |
| | Grade 3: 11/114 | Grade 3: 6/114 |
| | Grade 4: 1/114 | Grade 4: 0/114 |
| | Grade 5: 2/114 | Grade 5: 0/114 |

* = 1 calf received 1 pellet.
** = 2 calves received 1 pellet.
**** = 4 calves received 1 pellet.

We claim:

1. A method for vaccinating cattle with an immunogen for providing a protective immune response against at least one of a bacteria, a virus or a protozoa, said method comprising the step of implanting a biologically active pellet containing an effective immune stimulating amount of said immunogen subcutaneously into an ear of said cattle.

2. The method of claim 1 wherein the biologically active pellet comprises about 45 to 97% by weight of the said immunogen.

3. The method of claim 1 wherein the biologically active pellet comprises:

(a) about 45 to 97% by weight of the said immunogen;

(b) about 2 to 40% by weight of a freeze drying excipient; and (c) about 0.2 to 5% by weight of a lubricant.

4. The method of claim 1 wherein the said immunogen is selected from the group consisting of infectious bovine rhinotracheitis virus, bovine viral diarrhea virus, bovine parainfluenza 3 virus, bovine respiratory syncytial virus, *Haemophilus somnus, Pasteurella haemolytica, Pasteurella multocida, Leptospira spp., Campylobacter fetus, Clostridium spp.*, rotavirus, coronavirus, *Escherichia coli, Moraxella bovis, Bordetella bronchiseptica, Erysipelothrix rhusiopathiae, Actinobacillus pleuropneumoniae, Mycoplasma hyopneumoniae, Mycoplasma bovis, Mycoplasma dispar*, porcine parvovirus, transmissible gastroenteritis virus, pseudorabies virus, *Salmonella spp.*, canine parvovirus, canine adenovirus, canine distemper, canine parainfluenza, and rabies.

5. The method of claim 1 wherein the said immunogen is selected from the group consisting of *Clostridium chauvoei, Clostridium septicium, Clostridium novyi, Clostridium sordellii*, and *Clostridium perfringens* and mixtures thereof.

6. The method of claim 1 wherein the said immunogen is *Clostridium perfringens* bacterin-toxoid and mixtures thereof.

7. A method for vaccinating cattle with an immunogen for providing a protective immune response against at least one of a bacteria, a virus or a protozoa said method comprising the step of implanting a biologically active pellet containing an effective immune stimulating amount of said immunogen subcutaneously into an ear of said cattle with an implant gun wherein the biologically active pellet comprises:

(a) about 45 to 97% by weight of said immunogen;

(b) about 2 to 40% by weight of a freeze drying excipient; and (c) about 0.2 to 5% by eight of a lubricant, wherein the biologically active pellet is about 0.13" to 0.17" in length and about 0.10" to 0.14" in diameter.

8. The method of claim 7 wherein the said immunogen is selected from the group consisting of *Clostridium chauvoei, Clostridium septicium, Clostridium novyi, Clostridium sordellii*, and *Clostridium perfringens* and mixtures thereof.

9. The method of claim 7 wherein the said immunogen is *Clostridium perfringens* bacterin-toxoid and mixtures thereof.

* * * * *

UNITED STATES PATENT AND TRADEMARK OFFICE
CERTIFICATE OF CORRECTION

PATENT NO. : 5,665,363

DATED : SEPTEMBER 9, 1997

INVENTOR(S) : HANSEN ET AL.

It is certified that error appears in the above-identified patent and that said Letters Patent is hereby corrected as shown below:

Col. 1, line 7: "Dec. 12, 1994" should read –Dec. 15, 1994—

Col. 5, line 29: insert – excipients comprise less—after the word "additional"

Col. 5, line 30: delete "less than about 50%" after the numeral "50%"

Col. 10, lines 20–21, claim 4: delete "*Bordetella bronchiseptica, Erysipelothrix rhusiopathiae, Actinobacillus pleuropneumoniae, Mycoplasma hyopneumoniae,*" after the word "*bovis*"

Col. 10, lines 23–24, claim 4: delete "porcine parvovirus, transmissible gastroenteritis virus, pseudorabies virus," after the word "*dispar,*"

Col. 10, line 24, claim 4: insert –and—before the word "*Salmonella*"

Col. 10, lines 24–26, claim 4: delete ", *canine parvovirus, canine adenovirus, canine distemper, canine parainfluenza, and rabies*" after the word "*spp.*"

Signed and Sealed this

Twelfth Day of January, 1999

Attest:

Attesting Officer

*Acting Commissioner of Patents and Trademarks*